United States Patent [19]

Horstmann et al.

[11] Patent Number: 4,920,141

[45] Date of Patent: Apr. 24, 1990

[54] SYNERGISTIC BIOCIDES OF CERTAIN NITROIMIDAZOLES AND ALDEHYDES

[75] Inventors: Dennis G. Horstmann, St. Louis; Douglas S. Jones, Kirkwood, both of Mo.

[73] Assignee: Petrolite Corporation, St. Louis, Mo.

[21] Appl. No.: 159,793

[22] Filed: Feb. 24, 1988

Related U.S. Application Data

[63] Continuation-in-part of Ser. No. 916,761, Oct. 5, 1986, abandoned.

[51] Int. Cl.$^5$ .................... A01N 35/00; A01N 35/02; A01N 43/50
[52] U.S. Cl. .................................. 514/398; 514/697; 514/705
[58] Field of Search .................. 514/398, 697, 705

[56] References Cited

U.S. PATENT DOCUMENTS

| | | | |
|---|---|---|---|
| 3,991,200 | 11/1976 | Berkelhammer et al. | 514/363 |
| 4,031,232 | 6/1977 | Winkelmann et al. | 514/398 |
| 4,072,749 | 2/1978 | Maestrone et al. | 514/398 |
| 4,395,341 | 7/1983 | Muir | 252/8.554 |
| 4,608,183 | 8/1986 | Rossmoore | 252/36 |
| 4,661,503 | 4/1987 | Martin et al. | 514/372 |
| 4,661,517 | 4/1987 | Martin et al. | 514/515 |
| 4,661,518 | 4/1987 | LaMarre et al. | 514/528 |

FOREIGN PATENT DOCUMENTS 2103928  3/1983  United Kingdom .

OTHER PUBLICATIONS

The Merck Index, 10th Ed., p. 641 (1983).

*Primary Examiner*—Allen J. Robinson
*Attorney, Agent, or Firm*—Robert E. Wexler; Stanley M. Tarter

[57] ABSTRACT

A mixture of bactericides of nitroimidazoles, particularly 1,2-dimethyl-5-nitro-1H-imidazole, or salts thereof and aldehydes, particularly glutaraldehyde and formaldehyde, has been found to exhibit synergistic results in inhibiting the growth of sulfate-reducing bacteria.

8 Claims, No Drawings

SYNERGISTIC BIOCIDES OF CERTAIN NITROIMIDAZOLES AND ALDEHYDES

CROSS REFERENCE TO RELATED APPLICATIONS

This application is a continuation-in-part application of U.S. patent application Ser. No. 916,761, filed Oct. 5, 1986 (now abandoned).

BACKGROUND OF THE INVENTION

1. Field of the Invention

This invention relates to bactericidal compositions comprising certain nitroimidazoles or their salts, together with at least one aldehyde, and to industrial compositions containing such bactericidal compositions and to the use of such bactericidal compositions for inhibiting and controlling the growth of microorganisms, such as sulfate-reducing bacteria (SRB) in industrial aqueous liquids containing organic materials. More particularly, the invention relates to the use of bactericidal nitroimidazoles or their salts in conjunction with bactericidal aldehydes for inhibiting and controlling the growth of bacteria in industrial aqueous liquids containing organic materials.

The presence of sulfate-reducing bacteria (SRB) in liquid organic materials and aqueous liquids containing organic materials is a serious industrial problem, since such bacteria metabolize reductively sulfates and sulfonates with the liberation of hydrogen sulfide. Such metabolism results in foul smells and corrosion caused by the liberated hydrogen sulfide. The presence of SRB in hydrocarbon streams, vegetable oils, fuel oils, lubricating oils, mineral oil-based hydraulic fluids, O/W and W/O emulsions such as are used in metal working fluids and hydraulic fluids and in aqueous liquids containing such materials are examples of materials which are attacked by SRB. Examples of industrial liquids which are adversely affected by the presence of SRB include paper-pulp sulfite processing fluids, industrial process waters, electroplating solutions, oilwells, oilwell injection waters such as water floods, polymer floods, fracturing fluids and the like storage tanks used to store emulsions of water and oil and the like.

Since SRB action represents severe odor and corrosion problems in virtually all areas of industrial processing, industry is constantly searching for more effective bactericidal materials to inhibit and control the growth of SRB.

2. Description of Prior Art

Various materials have heretofore been used to inhibit the growth of SRB in industrial liquids. Such known bactericides include nitroimidazoles, aldehydes, isothiazolones, phenolics, heavy metal compounds, acrolein and others. All of these known bactericidal materials are effective against SRB in varying degrees but all prepsent certain problems relating to their use. Thus, some of the materials present toxicity problems, some of the materials are very expensive to use, others present solubility problems in aqueous liquids, others are not compatible with desired or required chemical additives and others remain as residues in water in sufficiently high concentrations to render the water toxic. Certain of the materials are quite corrosive to metals.

Insofar as the present invention is concerned, U.S. Pat. No. 2,944,061 discloses the use of salts of 2-methyl-5-nitroimidazole-1-ethanol (metronidazole) in the treatment of amoebic and protozoal infestations. Further, U.S. Pat. No. 4,395,341 discloses the use of metronidazole as a bactericide in flood waters which are injected into oil bearing formations. Still further, UK Patent Application No. 2103928 discloses the use of various nitroimidazoles in inhibiting spoilage of liquid organic materials.

Although the nitroimidazoles disclosed by the prior art have been found to be effective against certain bacteria, e.g., SRB, the nitroimidazoles present the disadvantage of being, among other things, only sparingly soluble in water. Obviously, a bactericide which is to be used in aqueous liquids is easier to use, is less expensive and is more effective if it is readily soluble in the aqueous liquid.

The present invention provides nitroimidazole-aldehyde bactericial compositions which are highly effective in inhibiting and controlling the growth of SRB and the concomitant liberation of hydrogen sulfide.

Brief Summary of the Invention

It has been found, in accordance with the present invention, that nitroimidazoles and acid addition salts of nitroimidazoles are highly effective bactericides in inhibition of SRB. The salts are less expensive and easier to use, in view of their higher water solubility, than are the nitroimidazoles per se. The nitroimidazoles and acid addition salts used in the present invention are used in conjunction with bactericidal aldehydes. Specifically, it has been found that mixtures of the bactericides, nitroimidazoles or salts thereof and certain aldehydes, particularly glutaraldehyde and formaldehyde, exhibit synergistic bactericidal results, particularly in inhibiting the growth of SRB. More specifically, it has now been discovered that mixtures of (a) bactericidal nitroimidazoles and water soluble salts thereof having the formula

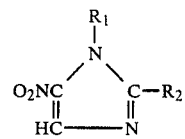

wherein $R_1$ and $R_2$ are selected from $C_1$–$C_5$ alkyl radicals and (b) a bactericidal aldehyde selected from the group consisting of formaldehyde and glutaraldehyde produce synergistic bactericidal effect in inhibiting and controlling the growth of SRB in oil field process water. The synergistic effect is better obtained when the weight ratio of imidazole to aldehyde in the mixture is in the range of about 1:2 to 1:100. The preferred mixtures are those containing 1,2-dimethyl-5-nitroimidazole or bactericidally acceptable salts thereof and either glutaraldehyde or formaldehyde.

Another aspect of the present invention contemplates the method of adding the synergistic mixtures of imidazoles and aldehydes as disclosed herein in bactericidally effective amounts to aqueous media, particularly oil field process water, infested with bacteria.

Detailed Description of the Invention

The bactericides used in the present invention in combination with aldehydes include but are not limited to the following compounds or salts thereof:

1-(2-hydroxyethyl)-2-methyl-5-nitroimidazole (metronidazole), 1,2-dimethyl-5-nitro-1H-imidazole (dimetridazole), 1-(2-hydroxypropyl)-2-methyl-5-nitroimidazole (secnidazole) and 1-methyl-2isopropyl-5-nitroimidazole (ipronidazole).

The salts of the above-referred to nitroimidazoles include the acid addition salts such as the hydrohalides, e.g., hydrochloride, hydrobromide and hydroiodide, phosphates, nitrates, sulfates, acetates, propionates, maleates, fumerates, citrates, tartrates, adipates, methane sulfonates, ethane disulfonates and the like and also include the ammonium salts and quaternary ammonium salts. The strong acid mineral salts are preferred.

The nitroimidazole compounds used in the present invention are known compounds and their methods of preparation are well known to those skilled in the art. Similarly, the acid addition salts, ammonium salts and quaternary ammonium salts are likewise easily prepared by those skilled in the art.

Compositions containing the two bactericides, i.e. imidazole and aldehyde, may be prepared in a number of conventional ways. 1,2-Dimethyl-5-nitro-1H-imidazole is freely soluble in methanol but only sparingly soluble in cold water. However, the hydrochloride salt of the imidazole is soluble in both water and methanol. Formaldehyde gas is soluble in water up to about 37% by weight and glutaraldehyde is soluble in water. Formulations or compositions for injection into SRB contaminated water may be prepared, for instance by mixing suitable amounts of each of the bactericide in water or a mixture of alcohol and water. The amounts of water, aldehyde and imidazole are selected so as to provide solutions containing the desired weight ratio of nitroimidazole and aldehyde for incorporation into the SRB infected medium at the desired rate.

Control of SRB infestation is possible at a rate as low as 0.1 ppm to about 25 ppm total active ingredients. It is to be understood that it may be necessary to employ substantially higher rates depending on the degree of control needed, the type of media, and the type of bacteria to be controlled.

The following examples illustrate specific, nonlimiting embodiments of the invention, including the best mode of practice of the invention.

In the following examples the bacteriostatic screen test for determining inhibition of SRB was conducted following the American Petroleum Institute (API) Recommended Practice (RP) No. 38 for Biological Analysis of Subsurface Injection Waters which generally is as follows:

1. Assemble two rows each containing six sulfate API broth vials (9.0 ml each).
2. Transfer 0.1–0.5 ml of test compound solution from an appropriate stock solution to produce the following final concentrations in the sulfate API broth vials: 0, 10, 20, 40, 80 and 160 ppm (shake vials to insure uniform dispersion of test solution).
3. Innoculate each test vial including control with 0.5 ml of a 24-hour culture of "field strain" SRB.
4. Incubate for the indicated number of days at 35° C. Record results after the indicated period of time. Blackening resulting from the presence of iron sulfide indicates growth of SRB. Bacteriostatic activity level is the lowest concentration showing no blackening, since the API procedure uses an extinction technique.

In the test determination herein of the activity of the test formulations in regard to inhibiting the growth of SRB unless otherwise indicated the broth composition employed was the sulfate-reducer medium as set-forth the API RP38. In the determination of the activity of the test formulations in inhibiting the growth of anaerobes, the broth composition used was the standard thioglycollate broth. A development of a uniform turbidity in the medium indicates the presence of anaerobes with the bacteriostatic level of the test formulations being the lowest concentration showing no turbidity. In the determination of the activity of the test formulations in inhibiting the growth of aerobes, the broth composition used was the standard phenol red dextrose broth. A change in the color of broth from red to yellow indicates the presence of aerobes with the bacteriostatic level of the test formulation being the lowest concentration showing no color change.

The measurement of surviving bacteria per unit volume was determined by the adenosine triphosphate (ATP) method. ATP is an energy-storing molecule containing high energy bonds found in all living cells. The presence of ATP can be measured by the use of an instrument called an ATP photometer. It measures the amount of light produced from the reaction of ATP and an enzyme system based on luciferin/luciferase, extracted from the tails of fireflies. The energy level as determined by the photometric measurement indicates with considerable accuracy the total biomass within a sample. It, however, does not distinguish the type of microorganism such as the presence of fungal and algal cells together with bacterial cells.

EXAMPLE 1

In this example, the effectiveness of dimetridazole hydrochloride for inhibiting the growth of SRB and anaerobic bacteria is demonstrated and compared against dimetridazole and metronidazole. The results are set-forth in Table 1 which presents data generated from a laboratory test showing inhibition of hydrogen sulfide production and bactericidal activity against SRB. The test was set up using a modified sulfate API broth as the test medium. The test medium was purged with argon to remove dissolved oxygen and dispensed into 100 ml argon purged serum vials. They were then sterilized. Various concentrations of metronidazole, dimetridazole and dimetridazole hydrochloride were made from 1% solutions. Each vial was inoculated with 2 ml of a 1–10 dilution of a 24-hour old culture of "field seed" SRB. After 1, 2 and 7 days of exposures, the levels of surviving SRB and concentrations of hydrogen sulfide were measured.

The data are tabulated in Table 1.

TABLE 1

| | Comparison of Inhibitory Activity Against Sulfate Reducing Bacteria | | | | | | |
|---|---|---|---|---|---|---|---|
| | Concentration | Exposure Time[d] | | | | | |
| | of Active Ingre- | 1 Day | | 2 Days | | 7 Days | |
| Compound | dient (ppm) | SRB/ml[b] | $H_2S$ (ppm)[c] | SRB/ml | $H_2S$ (ppm) | SRB/ml | $H_2S$ (ppm) |
| Metronidazole | 0.4 | >100 | 0.5 | 10–100 | 0.5 | >100 | 20 |
| | 0.8 | 0 | 0.5 | 0 | 0.5 | >100 | 0.5 |
| | 1.6 | 0 | 0.5 | 0 | 0.5 | 0 | 0.5 |

TABLE 1-continued

| Compound | Concentration of Active Ingredient (ppm) | Exposure Time[a] | | | | | |
|---|---|---|---|---|---|---|---|
| | | 1 Day | | 2 Days | | 7 Days | |
| | | SRB/ml[b] | H$_2$S (ppm)[c] | SRB/ml | H$_2$S (ppm) | SRB/ml | H$_2$S (ppm) |
| Dimetridazole | 0.3 | 0 | 0.5 | 10-100 | 0.5 | >100 | 15 |
| | 0.6 | 0 | 0.5 | 0 | 0.5 | 0 | 0.5 |
| | 1.2 | 0 | 0.5 | 0 | 0.5 | 0 | 0.5 |
| Dimetridazole | 0.3 | 0 | 0.5 | 0 | 0.5 | >100 | 20 |
| Hydrochloride | 0.6 | 0 | 0.5 | 0 | 0.5 | 0 | 0.5 |
| | 1.2 | 0 | 0.5 | 0 | 0.5 | 0 | 0.5 |
| Control | — | >100,000 | 4.5 | >100,000 | 16 | >100,000 | 20 |
| | 0.5 ppm H$_2$S | | | | | | |
| | 100,000 SRB/ml | | | | | | |

[a]Test rechallenged with SRB after the 1 and 2 day exposure times
[b]SRB enumerated by the extinction diluton technique
[c]H$_2$S levels measured by the Hach-Alka Seltzer method The data is Table 1 illustrate that dimetridazole hydrochloride is a potent inhibitor of hydrogen sulfide production caused by SRB. It was also bactericidal, giving complete kill of SRB at 0.6 ppm active ingredient even after repeated rechallenging with bacteria. For comparison, 1.6 ppm active metronidazole was required for complete kill of SRB after seven days exposure.

EXAMPLE 2

This example presents the results of a field kill test carried out at a commercial water plant. The produced water at the plant was a moderate brine and contained about 40 ppm hydrogen sulfide. The produced water was dispensed into 50 ml argon purged serum vials. Various concentrations of dimetridazole and dimetridazole hydrochloride were made. After 24-hour exposure, levels of SRB, anaerobic bacteria and total bacteria by ATP were measured. The results are tabulated in Table 2.

TABLE 2

| Comparison of Bactericidal Activity[a] | | | | |
|---|---|---|---|---|
| Compound | Active Ingredient (ppm) | Surviving Bacteria/ml | | |
| | | Sulfate Reducers | Anaerobic | ATP Method |
| Dimetridazole | 3 | 10-100 | >100 | 16,000,000 |
| | 6 | 10-100 | >100 | 8,700,000 |
| | 12 | 10-100 | >100 | 9,800,000 |
| | 24 | 10-100 | 10-100 | 14,000,000 |
| Dimetridazole | 3 | 10-100 | >100 | 6,900,000 |
| Hydrochloride | 6 | 10-100 | >100 | 6,500,000 |
| | 12 | 10-100 | >100 | 11,000,000 |
| | 24 | 1-10 | 10-100 | 7,300,000 |
| Control | — | >100 | >100 | 6,400,000 |

[a]Test Solution: Produced water from commercial water plant clear tank
Exposure Time: 24 Hrs.

The results illustrated in Table 2 show that levels of up to 24 ppm active dimetridazole had no effect on bacteria present in the produced water. The dimetridazole hydrochloride reduced SRB levels by at least 90 percent at 24 ppm active concentration.

EXAMPLE 3

This example shows the synergism obtained by employing the combination of an imidazole bactericide and glutaraldehyde at various active ingredient levels as compared with employing the same imidazole alone or aldehyde alone. In the example, the aqueous medium containing the SRB was an Illinois oil field flood water. The initial count of total bacteria per ml in the control was determined to be $6.0 \times 10^6$ by the ATP procedure. At 1, 7, 14 and 25 days after treatment (DAT), SRB, anaerobes and aerobes in the media were determined by the API RP38 procedure; and the total count of bacteria was determined by the ATP procedure. The results of these determinations are set forth in Table 3 below. In formulation 1 the active imidazole ingredient was 1,2-dimethyl-5-nitroimidazole and was formualted as a solution of 1% active, 35% methanol and 64% water. In formualtion 2 active imidazole ingredient was 1,2-dimethyl-5-nitroimidazole and the active aldehyde ingredient was glutaraldehyde. The formulation of the mixture was 20% glutaraldehyde, 0.5% 1,2-dimethyl-5-nitroimidazole and 79.5% water. In formulation 3 the active aldehyde ingredient was glutaraldehyde and was formulated as a 25% aqueous solution.

TABLE 3

| FORMULATION NO. | IMIDAZOLE PPM | ALDEHYDE PPM | SURVIVING BACTERIA/ML | | | | |
|---|---|---|---|---|---|---|---|
| | | | DAT | SRB | ANAEROBES | AEROBES | TOTAL $\times 10^6$ BY ATP | % KILL |
| 1. | 0.25 | 0 | 1 | >100 | >100 | >100 | 7.5 | 0 |
| | 0.5 | 0 | 1 | >100 | >100 | >100 | 6.6 | 0 |
| | 1.0 | 0 | 1 | >100 | >100 | >100 | 6.8 | 0 |
| | 2.0 | 0 | 1 | >100 | >100 | >100 | 6.8 | 0 |
| | 0.25 | 0 | 7 | 10-100 | >100 | >100 | 2.3 | 61.7 |
| | 0.5 | 0 | 7 | 10-100 | >100 | >100 | 1.8 | 70.0 |
| | 1.0 | 0 | 7 | 10-100 | >100 | >100 | 1.6 | 73.3 |
| | 2.0 | 0 | 7 | 10-100 | >100 | >100 | 1.4 | 76.7 |
| | 0.25 | 0 | 14 | 10-100 | >100 | >100 | 2.3 | 61.7 |
| | 0.5 | 0 | 14 | 10-100 | >100 | >100 | 1.4 | 76.7 |
| | 1.0 | 0 | 14 | 10-100 | >100 | >100 | 0.77 | 87.2 |
| | 2.0 | 0 | 14 | 10-100 | >100 | >100 | 2.0 | 66.7 |
| | 0.25 | 0 | 25 | 0 | >100 | >100 | 0.57 | 90.5 |
| | 0.5 | 0 | 25 | 100 | >100 | >100 | 0.43 | 92.8 |

TABLE 3-continued

| FORMULATION NO. | IMIDAZOLE PPM | ALDEHYDE PPM | SURVIVING BACTERIA/ML | | | | | |
|---|---|---|---|---|---|---|---|---|
| | | | DAT | SRB | ANAEROBES | AEROBES | TOTAL × 10⁶ BY ATP | % KILL |
| | 1.0 | 0 | 25 | 10-100 | >100 | >100 | 0.39 | 93.5 |
| | 2.0 | 0 | 25 | 1-10 | >100 | >100 | 0.42 | 93.0 |
| 2. | 0.125 | 5 | 1 | 1-10 | 10-100 | 0 | 1.6 | 73.3 |
| | 0.25 | 10 | 1 | 0 | 0 | 0 | 2.0 | 66.7 |
| | 0.5 | 20 | 1 | 0 | 1-10 | 0 | 2.1 | 65.0 |
| | 1.0 | 40 | 1 | 0 | 0 | 0 | 2.3 | 61.7 |
| | 0.125 | 5 | 7 | 0 | 0 | 0 | 0.098 | 98.4 |
| | 0.25 | 10 | 7 | 0 | 0 | 1-10 | 0.34 | 94.3 |
| | 0.5 | 20 | 7 | 0 | 0 | 0 | 0.66 | 89.0 |
| | 1.0 | 40 | 7 | 0 | 0 | 0 | 1.3 | 78.3 |
| | 0.125 | 5 | 14 | 0 | 0 | 1-10 | 0.24 | 96.0 |
| | 0.25 | 10 | 14 | 0 | 1-10 | 0 | 0.074 | 98.8 |
| | 0.5 | 20 | 14 | 1-10 | 0 | 0 | 0.23 | 96.2 |
| | 1.0 | 40 | 15 | 0 | 1-10 | 0 | 0.60 | 90.0 |
| | 0.125 | 5 | 25 | 1-10 | 10-100 | 10-100 | 0.35 | 94.2 |
| | 0.25 | 10 | 25 | 0 | >100 | >100 | 0.10 | 98.3 |
| | 0.5 | 20 | 25 | 0 | 0 | 0 | 0.092 | 98.5 |
| | 1.0 | 40 | 25 | 0 | 0 | 0 | 0.020 | 99.7 |
| 3. | 0 | 5 | 1 | 10-100 | 1-10 | >100 | 1.9 | 68.3 |
| | 0 | 10 | 1 | 10-100 | 1-10 | 10-100 | 2.1 | 65.0 |
| | 0 | 20 | 1 | 1-10 | 0 | 10-100 | 3.5 | 58.3 |
| | 0 | 40 | 1 | 0 | 0 | 0 | 1.9 | 68.3 |
| | 0 | 5 | 7 | 10-100 | 1-10 | 0 | 2.0 | 66.7 |
| | 0 | 10 | 7 | 1-10 | 1-10 | 0 | 2/0 | 66.7 |
| | 0 | 20 | 7 | 0 | 10-100 | 0 | 1.8 | 70.0 |
| | 0 | 40 | 7 | 0 | 0 | 0 | 1.4 | 76.7 |
| | 0 | 5 | 14 | >100 | 1-10 | 1-10 | 0.92 | 84.7 |
| | 0 | 10 | 14 | 10-100 | 10-100 | 0 | 1.2 | 80.0 |
| | 0 | 20 | 14 | 0 | 1-10 | 0 | 0.75 | 87.5 |
| | 0 | 40 | 14 | 0 | 0 | 0 | 0.41 | 93.2 |
| | 0 | 5 | 25 | 100 | 1-10 | 10-100 | 2.5 | 60.0 |
| | 0 | 10 | 25 | 100 | 10-100 | >100 | 2.6 | 56.7 |
| | 0 | 20 | 25 | 100 | 10-100 | 10-10000 | 2.9 | 51.7 |
| | 0 | 40 | 25 | 0 | 0 | 0 | 0.93 | 84.5 |
| CONTROLS | | | 1 | >100 | >100 | >100 | 9.2 | |
| | | | 1 | >100 | >100 | >100 | 8.3 | |
| | | | 7 | >100 | >100 | >100 | 6.0 | |
| | | | 7 | >100 | >100 | >100 | 5.3 | |
| | | | 14 | >100 | >100 | >100 | 4.0 | |
| | | | 14 | >100 | >100 | >100 | 3.7 | |
| | | | 25 | >100 | >100 | >100 | 1.2 | |
| | | | 25 | >100 | >100 | >100 | — | |

The above data indicate, among other things, that the mixture of glutaraldehyde and 1,2-dimethyl-5-nitroimidazole was superior to glutaraldehyde used alone and 1,2-dimethyl-5-nitroimidazole used alone. Even at one day after treatment, the mixture of 25 ppm active provided in the test media SRB counts as compared to when each of the components were used alone. It should also be noted that aerobic bacteria were substantially killed at one day after treatment while glutaraldehyde used alone and dimetridazole used alone were substantially less effective.

EXAMPLE 4

This example shows the synergism obtained by employing the combination of an imidazole and formaldehyde at various levels of the active ingredients as compared to employing the same imidazole alone. In the example the aqueous medium containing the SRB was an Illinois oil field flood water. The initial count of bacteria in the control was determined to be $6.0 \times 10^6$ by the ATP procedure. At 1, 7, 14 and 25 days after the bactericidal compositions were added to the aqueous test media, SRB, anaerobes and aerobes in the media were determined by the API RP38 procedure and the total count of bacteria was determined by the ATP procedure. The results of these determinations are set forth in Table 4 below. Formulation 1 included 1% 1,2-dimethyl-5-nitroimidazole, 35% methanol and 64% water. In formulation 2 the active ingredients were formulated as an aqueous solution of 37% formaldehyde and 0.5% 1,2-dimethyl-5-nitroimidazole. Formulation No. 3 was an aqueous solution of 37% formaldehyde.

TABLE 4

| FORMULATION NO. | IMIDAZOLE PPM | ALDEHYDE PPM | SURVIVING BACTERIA/ML | | | | | |
|---|---|---|---|---|---|---|---|---|
| | | | DAT | SRB | ANAEROBES | AEROBES | TOTAL × 10⁶ BY ATP | % KILL |
| 1. | 0.25 | 0 | 1 | >100 | >100 | >100 | 7.5 | 0 |
| | 0.5 | 0 | 1 | >100 | >100 | >100 | 6.6 | 0 |
| | 1.0 | 0 | 1 | >100 | >100 | >100 | 6.8 | 0 |
| | 2.0 | 0 | 1 | >100 | >100 | >100 | 6.8 | 0 |
| | 0.25 | 0 | 7 | 10-100 | >100 | >100 | 2.3 | 61.7 |
| | 0.5 | 0 | 7 | 10-100 | >100 | >100 | 1.8 | 70.0 |
| | 1.0 | 0 | 7 | 10-100 | >100 | >100 | 1.6 | 73.3 |
| | 2.0 | 0 | 7 | 10-100 | >100 | >100 | 1.4 | 76.7 |

TABLE 4-continued

| FORMULATION NO. | IMIDAZOLE PPM | ALDEHYDE PPM | DAT | SURVIVING BACTERIA/ML SRB | ANAEROBES | AEROBES | TOTAL × 10⁶ BY ATP | % KILL |
|---|---|---|---|---|---|---|---|---|
| | 0.25 | 0 | 14 | 10-100 | >100 | >100 | 2.3 | 61.7 |
| | 0.5 | 0 | 14 | 10-100 | >100 | >100 | 1.4 | 76.7 |
| | 1.0 | 0 | 14 | 10-100 | >100 | >100 | 0.77 | 87.2 |
| | 2.0 | 0 | 14 | 10-100 | >100 | >100 | 2.0 | 66.7 |
| | 0.25 | 0 | 25 | 0 | >100 | >100 | 0.57 | 90.5 |
| | 0.5 | 0 | 25 | 100 | >100 | >100 | 0.43 | 92.8 |
| | 1.0 | 0 | 25 | 10-100 | >100 | >100 | 0.39 | 93.5 |
| | 2.0 | 0 | 25 | 1-10 | >100 | >100 | 0.42 | 93.0 |
| 2. | 0.125 | 9.25 | 1 | 1-10 | 10-100 | 10-100 | 1.3 | 78.3 |
| | 0.25 | 18.5 | 1 | 0 | 1-10 | 0 | 1.4 | 76.7 |
| | 0.5 | 37.0 | 1 | 0 | 1-10 | 1-10 | 1.8 | 70.0 |
| | 1.0 | 74.0 | 1 | 0 | 0 | 0 | 1.9 | 68.3 |
| | 0.125 | 9.25 | 7 | 0 | >100 | 1-10 | 0.45 | 92.5 |
| | 0.25 | 18.5 | 7 | 1-10 | >100 | >100 | 0.20 | 96.7 |
| | 0.5 | 37.5 | 7 | 0 | 1-10 | 0 | 1.3 | 78.3 |
| | 1.0 | 74.0 | 7 | 0 | 1-10 | 0 | 1.5 | 75.0 |
| | 0.125 | 9.25 | 14 | 0 | >100 | 10-100 | 0.93 | 84.5 |
| | .25 | 18.5 | 14 | 0 | >100 | >100 | 0.57 | 90.5 |
| | 0.5 | 37.0 | 14 | 0 | 0 | 0 | 0.78 | 87.0 |
| | 1.0 | 74.0 | 15 | 0 | 0 | 0 | 1.2 | 80.0 |
| | 0.125 | 9.25 | 25 | 1-10 | >100 | >100 | 0.62 | 89.7 |
| | 0.25 | 18.5 | 25 | 0 | >100 | >100 | 0.67 | 88.8 |
| | 0.5 | 37.0 | 25 | 0 | >100 | >100 | 0.24 | 96.0 |
| | 1.0 | 74.0 | 25 | 0 | >100 | >100 | 0.22 | 96.3 |
| 3. | 0 | 37 | 1 | 1-10 | 1-10 | 0 | 1.6 | 73.3 |
| | 0 | 74 | 1 | 0 | 0 | 0 | 1.9 | 68.3 |
| | 0 | 148 | 1 | 0 | 1-10 | 0 | 1.9 | 68.3 |
| | 0 | 37 | 7 | 0 | >100 | >100 | 0.76 | 87.3 |
| | 0 | 74 | 7 | 0 | 0 | 1-10 | 1.3 | 78.3 |
| | 0 | 148 | 7 | 0 | 0 | 0 | 1.5 | 75.0 |
| | 0 | 37 | 14 | 1-10 | >100 | >100 | 1.2 | 80.0 |
| | 0 | 74 | 14 | 0 | 0 | 1-10 | LOST | |
| | 0 | 148 | 14 | 0 | 0 | 0 | 1.0 | 83.3 |
| | 0 | 37 | 25 | >100 | >100 | >100 | 3.1 | 48.3 |
| | 0 | 74 | 25 | >100 | >100 | >100 | 3.9 | 35.0 |
| | 0 | 148 | 25 | 0 | >100 | >100 | 0.19 | 96.8 |
| CONTROLS | | | 1 | >100 | >100 | >100 | 9.2 | |
| | | | 1 | >100 | >100 | >100 | 8.3 | |
| | | | 7 | >100 | >100 | >100 | 6.0 | |
| | | | 7 | >100 | >100 | >100 | 5.3 | |
| | | | 14 | >100 | >100 | >100 | 4.0 | |
| | | | 14 | >100 | >100 | >100 | 3.7 | |
| | | | 25 | >100 | >100 | >100 | 1.2 | |
| | | | 25 | >100 | >100 | >100 | — | |

The above data indicate that the bactericidal activity of the mixtures of imidazoles and aldehydes are surprisingly greater than the additive effect of the ingredients when used singly. The mixtures of Examples 3 and 4 contain 0.5% by weight. 1,2-dimethyl-5-nitroimidazole. This is one-half the amount present in the formulations containing only 1,2-dimethyl-5-nitroimidazole. The bactericidal activity of the mixture is greater than the additive effect of the individual components of the mixture. Thus, the data indicate that the mixtures are synergistic.

It is contemplated that the salts of metronidazole, ipronidazole and secnidazole would be similarly effective and that, in addition to the hydrochloride salt as illustrated in the above examples, the hydrobromide, hydroiodide and the phosphates, nitrates, sulfates, acetates, propionates, maleates, fumerates, citrates, adipates, tartrates, methane sulfonates, and ethane disulfonates ammonium salts and quaternary ammonium salts would be similarly effective.

The nitroimidazole salts may be used in conjunction with other bactericides including compounds which liberate aldehydes, phenols, e.g., p-chloro-cresol and phenol, heavy metals, isothiazolones, mixtures of halogenated and non-halogenated isothiazolones and mixtures thereof. Bactericidal compositions containing the nitroimidazole salts of the present invention may be used in oil field and industrial hydrocarbon liquids, and in mixtures, dispersions or emulsions of hydrocarbon liquids, and in mixtures, dispersions or emulsions of hydrocarbon and aqueous liquids, for example, downhole injection waters such as water floods, polymer floods and fracturing fluids, oil-in-water and water-in-oil emulsions, gas transmission lines and storage fields, in hydrostatic testing of equipment such as tanks, vessels and pipe lines, in cutting and metal working fluids, in petroleum storage tanks and industrial process waters, in paper-pulp sulfite processing fluids, in electroplating solutions and in pipes, filters and other equipment used to produce, transport and store oil field and industrial process water liquids.

EXAMPLE 5

This example shows the synergism obtained by employing the combination an imidazole hydrochloride bactericide and certain aldehydes at various active ingredient levels as compared with employing the same imidazole alone or aldehydes alone. In this example, the aqueous medium containing the SRB was injection water from an Illinois oil field. The aqueous medium was a moderate brine of about 20,000 mg/l total dissolved solids and contained numerous SRB, anaerobes and aerobes. The average initial count of total bacteria per ml after one day in the control was determined to be $7.35 \times 10^5$ by the ATP procedure. At one and ten days after treatment (DAT), SRB, anaerobes and aerobes in the media were determined by the API RP38 procedure. The results of these determinations are set forth in Table 5 below. In formulation 1 the active imidazole ingredient was 1,2-dimethyl-5-nitroimidazole hydrochloride and was formulated as a solution of 1% active, 35% methanol and 64% water. In formulation 2 the active imidazole ingredient was 1,2-dimethyl-5-nitroimidazole hydrochloride and the active aldehyde ingredient was glutaraldehyde. The formulation of the mixture was 20% glutaraldehyde, 0.5% 1,2-dimethyl-5-nitroimidazole hydrochloride and 79.5% water. in formulation 3 the active imidazole ingredient was 1,2-dimethyl-5-nitroimidazole hydrochloride and the active aldehyde ingredient was formaldehyde. The formulation of the mixture was 37% formaldehyde and 0.5% 1,2-dimethyl-5-nitorimidazole hydrochloride and 62.5% water. In formulation 4 the active ingredient was glutaraldehyde formulated as a 25% aqueous solution thereof. In formualtion 5 the active ingredient was formaldehyde formulated as a 37% aqueous solution thereof. The control vials were prepared and contained no bactericide.

level, but SRB count was not reduced. Both aldehydes tested and blends with 1,2-dimethyl-5-nitroimidazole hydrochloride were relatively effective after one day's exposure. Formulation 3 was slightly more effective than formaldehyde alone.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and description set forth herein, but rather that the claims by construed as encompassing all the features of patentable novelty which reside in the present invention, including all features which would be treated as equivalents thereof by those skilled in the art to which the invention pertains.

What is claimed is:

1. A bactericidal composition useful in treating industrial process water to inhibit and control the growth of sulfate-reducing bacteria comprising a synergistic bactericidally effective amount of a mixture of (a) a water-soluble salt of metronidazole, dimetridazole, secnidazole or ipronidazole and (b) glutaraldehyde, the

TABLE 5

| FORMULATION NO. | IMIDAZOLE PPM | ALDEHYDE PPM | DAT | SURVIVING BACTERIA/ML | | | TOTAL $\times 10^6$ BY ATP | % KILL |
|---|---|---|---|---|---|---|---|---|
| | | | | SRB | ANAEROBES | AEROBES | | |
| 1. | 0.125 | 0 | 1 | >100 | >100 | 10–100 | 1.4 | 0 |
| | 0.250 | 0 | 1 | >100 | >100 | 10–100 | 1.2 | 0 |
| | 0.500 | 0 | 1 | >100 | >100 | >100 | 1.4 | 0 |
| | 1.000 | 0 | 1 | >100 | 0 | 10–100 | 0.67 | 0 |
| | 0.125 | 0 | 10 | >100 | >100 | 10–100 | 1.1 | 0 |
| | 0.250 | 0 | 10 | >100 | >100 | >100 | 1.4 | 0 |
| | 0.500 | 0 | 10 | >100 | >100 | >100 | 3.0 | 0 |
| | 1.000 | 0 | 10 | >100 | >100 | >100 | 0.94 | 0 |
| 2. | 0.125 | 5.0 | 1 | 10–100 | >100 | 0 | 0.13 | 82 |
| | 0.250 | 10.0 | 1 | 1–10 | 1–10 | 0 | 0.04 | 94 |
| | 0.500 | 20.0 | 1 | 0 | 0 | 0 | 0.06 | 92 |
| | 1.000 | 40.0 | 1 | 0 | 0 | 0 | 0.03 | 97 |
| | 0.125 | 5.0 | 10 | 1–10 | 10–100 | 0 | 1.3 | 0 |
| | 0.250 | 10.0 | 10 | 0 | 0 | 0 | 0.04 | 94 |
| | 0.500 | 20.0 | 10 | 0 | 1–10 | 0 | 0.04 | 94 |
| | 1.000 | 40.0 | 10 | 0 | 0 | 0 | 0.02 | 97 |
| 3. | 0.125 | 9.25 | 1 | 10–100 | 10–100 | 1–10 | 0.31 | 58 |
| | 0.250 | 18.5 | 1 | 0 | 0 | 0 | 0.06 | 92 |
| | 0.500 | 37.0 | 1 | 0 | 0 | 0 | 0.03 | 96 |
| | 1.000 | 74.0 | 1 | 0 | 0 | 0 | 0.03 | 96 |
| | 0.125 | 9.25 | 10 | 10–100 | >100 | 10–100 | 1.2 | 0 |
| | 0.250 | 18.5 | 10 | 0 | >100 | 0 | 2.5 | 0 |
| | 0.500 | 37.0 | 10 | 0 | 1–10 | 0 | 0.02 | 98 |
| | 1.000 | 74.0 | 10 | 0 | 1–10 | 0 | 0.03 | 96 |
| 4. | 0 | 5.0 | 1 | 10–100 | 10–100 | 1–10 | 0.09 | 88 |
| | 0 | 10.0 | 1 | 0 | 0 | 0 | 0.08 | 89 |
| | 0 | 20.0 | 1 | 0 | 0 | 0 | 0.03 | 96 |
| | 0 | 40.0 | 1 | 0 | 0 | 0 | 0.03 | 96 |
| | 0 | 5.0 | 10 | >100 | 1–10 | 10–100 | 8.5 | 0 |
| | 0 | 10.0 | 10 | >100 | 1–10 | 1–10 | 2.3 | 0 |
| | 0 | 20.0 | 10 | 1–10 | 0 | 0 | 0.14 | 81 |
| | 0 | 40.0 | 10 | 1–10 | 0 | 0 | 0.04 | 94 |
| 5. | 0 | 9.25 | 1 | >100 | >100 | 1–10 | 0.26 | 65 |
| | 0 | 18.5 | 1 | 0 | 0 | 0 | 0.06 | 91 |
| | 0 | 37.0 | 1 | 0 | 0 | 0 | 0.04 | 94 |
| | 0 | 74.0 | 1 | 0 | 0 | 0 | 0.03 | 95 |
| | 0 | 9.25 | 10 | 10–100 | >100 | >100 | 3.9 | 0 |
| | 0 | 18.5 | 10 | 0 | 1–10 | 0 | 1.5 | 0 |
| | 0 | 37.5 | 10 | 0 | 0 | 0 | 3.6 | 0 |
| | 0 | 74.0 | 10 | 0 | 1–10 | 0 | 0.03 | 96 |
| Controls | 0 | 0 | 10 | $10^3$–$10^4$ | $10^4$–$10^5$ | $10^4$–$10^5$ | 3.9 | — |
| | 0 | 0 | 10 | $10^3$–$10^4$ | $10^4$–$10^5$ | $10^3$–$10^4$ | 2.9 | — |

The above data indicate, among other things that 1,2-dimethyl-5-nitroimidazole hydrochloride was relatively ineffective. Some reduction in total bacteria count can be seen at the 1 ppm active concentration weight ratio of component (a) to component (b) being between about 1:2 to 1:100.

2. The composition of claim 1 where in the salt is a strong acid addition salt.

3. The composition of claim 2 wherein the salt is the hydrochloride salt.

4. The composition of claim 1 wherein component (a) is the water-soluble salt of metronidazole.

5. A method of inhibiting the growth of bacteria in an aqueous medium comprising adding to an aqueous medium comprising reducing bacteria a synergistic bactericidally effective amount of a mixture of (a) a water-soluble salt of metronidazole, dimethridazole, secnidazole or ipronidazole and (b) glutaraldehyde, the weight ratio of component (a) to component (b) being between about 1:2 to 1:100.

6. The method of claim 5 wherein the salt is a strong acid addition salt.

7. The method of claim 6 wherein the salt is the hydrochloride salt.

8. The method of claim 5 wherein component (a) is the water-soluble salt of metronidazole.

* * * * *

UNITED STATES PATENT AND TRADEMARK OFFICE
CERTIFICATE OF CORRECTION

PATENT NO. : 4,920,141

DATED : April 24, 1990

INVENTOR(S) : Dennis G. Horstmann and Douglas S. Jones

It is certified that error appears in the above-identified patent and that said Letters Patent is hereby corrected as shown below:

In Table 3, in Formulation No. 2, Column DAT, line 12, delete "15" and substitute therefore -- 14 --.

Signed and Sealed this

Eleventh Day of June, 1991

Attest:

HARRY F. MANBECK, JR.

*Attesting Officer*  *Commissioner of Patents and Trademarks*